(12) United States Patent
Tagawa et al.

(10) Patent No.: US 11,224,390 B2
(45) Date of Patent: Jan. 18, 2022

(54) RADIATION IMAGING APPARATUS

(71) Applicant: CANON KABUSHIKI KAISHA, Tokyo (JP)

(72) Inventors: Motoki Tagawa, Chigasaki (JP); Satoru Omura, Chigasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 89 days.

(21) Appl. No.: 16/520,858

(22) Filed: Jul. 24, 2019

(65) Prior Publication Data

US 2020/0037969 A1    Feb. 6, 2020

(30) Foreign Application Priority Data

Jul. 31, 2018    (JP) .............................. JP2018-144028

(51) Int. Cl.
| | | |
|---|---|---|
| *A61B 6/00* | (2006.01) | |
| *G01T 1/24* | (2006.01) | |
| *G01N 23/04* | (2018.01) | |
| *H04N 5/335* | (2011.01) | |
| *H01L 27/146* | (2006.01) | |
| *H01L 31/08* | (2006.01) | |

(52) U.S. Cl.
CPC .............. *A61B 6/44* (2013.01); *A61B 6/4283* (2013.01); *A61B 6/4405* (2013.01); *G01N 23/04* (2013.01); *G01T 1/244* (2013.01); *H01L 27/14601* (2013.01); *H01L 27/14618* (2013.01); *H04N 5/335* (2013.01); *H01L 31/085* (2013.01)

(58) Field of Classification Search
CPC ....... A61B 6/2483; A61B 6/44; A61B 6/4405; G01N 23/04; G01T 1/244; H01L 27/14601; H01L 27/14618; H01L 31/085; H04N 5/335
See application file for complete search history.

(56) References Cited

U.S. PATENT DOCUMENTS

| | | |
|---|---|---|
| 6,049,074 A | 4/2000 | Endo et al. |
| 8,754,380 B2 | 6/2014 | Omura |
| 9,275,770 B2 | 3/2016 | Omura |
| 9,295,438 B2 | 3/2016 | Omura et al. |
| 9,801,596 B2 | 10/2017 | Tagawa |
| 10,061,042 B2 | 8/2018 | Suzuki et al. |
| 10,073,180 B2 | 9/2018 | Kobayashi |
| 10,274,613 B2 | 4/2019 | Suzuki |
| 2012/0195404 A1 | 8/2012 | Omura |

(Continued)

FOREIGN PATENT DOCUMENTS

| | | |
|---|---|---|
| CN | 202009411 U | 10/2011 |
| CN | 204683229 U | 10/2015 |

(Continued)

*Primary Examiner* — Mark R Gaworecki
(74) *Attorney, Agent, or Firm* — Venable LLP (57) ABSTRACT

A radiation imaging apparatus comprises a radiation sensor configured to convert incident radiation to an electrical signal and a housing configured to encompass the radiation sensor, wherein a holding portion that is shaped as a recess is formed in a back face of the housing, the back face being on a side opposite to a radiation incident surface of the housing, and a member having a lower heat conductivity than a heat conductivity of the back face is arranged at a position corresponding to the holding portion in the back face.

19 Claims, 5 Drawing Sheets

(56) References Cited

U.S. PATENT DOCUMENTS

| | | | |
|---|---|---|---|
| 2012/0318991 A1* | 12/2012 | Ohta | A61B 6/4488 250/366 |
| 2014/0098942 A1 | 4/2014 | Omura et al. | |
| 2019/0011574 A1* | 1/2019 | Suwa | A61B 6/4488 |
| 2019/0110376 A1 | 4/2019 | Tagawa et al. | |

FOREIGN PATENT DOCUMENTS

| | | |
|---|---|---|
| CN | 105662442 A | 6/2016 |
| CN | 105997111 A | 10/2016 |
| CN | 106556613 A | 4/2017 |
| JP | H09-288184 A | 11/1997 |
| JP | 2013-200188 A | 10/2013 |
| JP | 2015-051206 | 3/2015 |
| JP | 2016-085063 | 5/2016 |
| JP | 2017-067564 A | 4/2017 |

* cited by examiner

RADIATION IMAGING APPARATUS

BACKGROUND OF THE INVENTION

Field of the Invention

The present invention relates to a radiation imaging apparatus.

Description of the Related Art

In recent years, apparatuses that acquire digital images using a semiconductor sensor (radiation sensor) have been increasingly used as radiation imaging apparatuses for use in medical image diagnosis and non-destructive inspection. Given the situation, improved operational efficiency has been achieved due to the ability to instantly check acquired images, unlike the case of acquiring images using a conventional photosensitive film. Furthermore, since images acquired using the radiation sensor have a very wide dynamic range, the use of the radiation sensor also enables imaging without being affected by a change in the amount of radiation exposure.

A radiation imaging apparatus that uses a radiation sensor contains a circuit board (integrated circuit) for controlling imaging operations and processing radiographic images, and this circuit board serves as a heat source. If heat generated by this heat source makes the temperature of the radiation sensor nonuniform in the surface thereof, there is concern that unevenness will occur in the images. It is therefore necessary to efficiently release the heat to the outside of an effective region of the radiation sensor. Japanese Patent Laid-Open No. 09-288184 discloses a structure that suppresses an increase in the temperature of the radiation sensor by providing a heat conduction member for thermally connecting a heat generating portion to a housing.

Also, portable imaging apparatuses have also been put into practical use due to a further decrease in the size and weight of imaging apparatuses. Imaging can be performed in any orientation, and such portable imaging apparatus are used for preference in radiation imaging in general hospital rooms or outside, for example. Japanese Patent Laid-Open No. 2017-067564 proposes a structure in which a holding portion is formed that is recessed in a surface on the side opposite to a radiation incident surface such that a portable apparatus is favorably holdable.

In recent years, there may be cases where power consumption during imaging increases due to an increase in the functionalities of imaging apparatuses. In this case, if heat generated within an imaging apparatus is released to a housing thereof, the temperature of the housing increases further, and there is a concern that an operator or a subject to be examined may feel uncomfortable when the apparatus is handled. In particular, a person is likely to feel uncomfortable if a portion of the imaging apparatus that the person holds for a long time feels hot.

SUMMARY OF THE INVENTION

In view of the foregoing problem, the present disclosure provides a structure of a radiation imaging apparatus with good holdability that makes an operator and a subject to be examined feel less uncomfortable.

According to one aspect of the present invention, there is provided a radiation imaging apparatus which comprises: a radiation sensor configured to convert incident radiation to an electrical signal; and a housing configured to encompass the radiation sensor, wherein a holding portion that is shaped as a recess is formed in a back face of the housing, the back face being on a side opposite to a radiation incident surface of the housing, and a member having a lower heat conductivity than a heat conductivity of the back face is arranged at a position corresponding to the holding portion in the back face.

According to another aspect of the present invention, there is provided a radiation imaging apparatus which comprises: a radiation sensor configured to convert incident radiation to an electrical signal; and a housing configured to encompass the radiation sensor, wherein a holding portion that is shaped as a recess is formed in a back face of the housing, the back face being on a side opposite to a radiation incident surface of the housing, and a member having a lower heat conductivity than a heat conductivity of the back face is arranged so as to cover the recess.

Further features of the present invention will become apparent from the following description of exemplary embodiments with reference to the attached drawings.

DESCRIPTION OF THE EMBODIMENTS

Hereinafter, embodiments of the present invention will be described in detail with reference to the attached drawings. However, the details of the dimensions and structures described in the embodiments are not limited to those described in the text and the drawings. Note that, in the present specification, not only X-rays but also α-rays, (β-rays, γ-rays, particle beams, cosmic rays, and the like are also included in radiation.

Embodiment 1

Configuration of Radiation Imaging System

Figure 1:
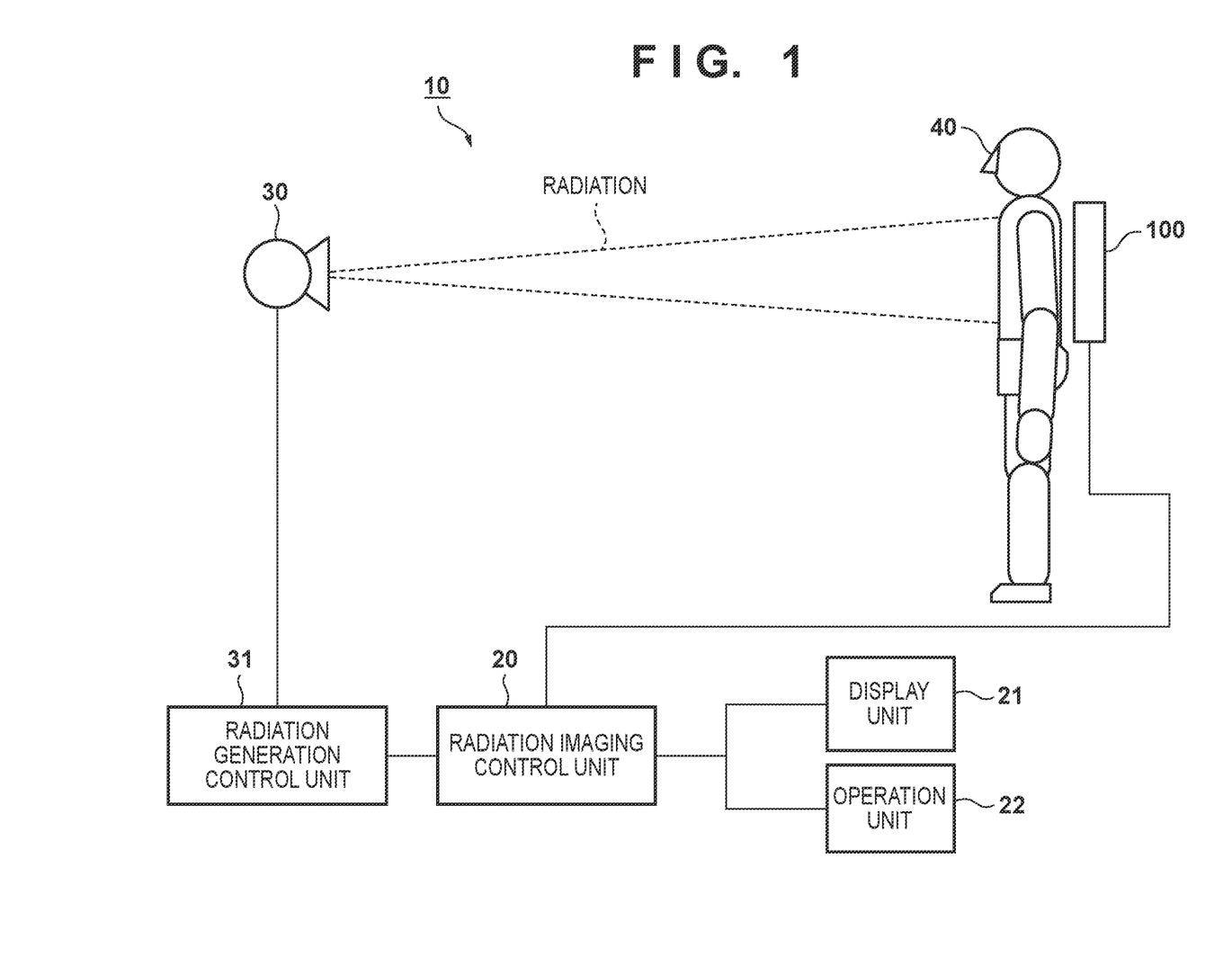
FIG. 1 shows an example configuration of a radiation imaging system according to Embodiment 1.

FIG. 1 shows an example configuration of a radiation imaging system 10 according to Embodiment 1. The radiation imaging system 10 is a system for imaging a digital radiation image (hereinafter referred to as "radiographic image"), and performs examination (imaging) based on an examination order, which includes a plurality of pieces of examination information. The examination information includes imaging protocol information, and imaging protocols defines parameter information or imaging implementation information to be used during imaging or in image processing, as well as imaging environment information, such as a sensor type or an imaging orientation. The examination information includes information that specifies an examination order or specifies a radiographic image according to the examination order, such as an examination ID and a receipt number.

The radiation imaging system 10 includes a radiation imaging apparatus 100, a radiation generation control unit 31, a radiation imaging control unit 20, a display unit 21, an operation unit 22, and a radiation source 30. The radiation source 30 functions as a radiation generation unit. That is to say, the radiation source 30 is an X-ray tube in this embodiment, and irradiates a subject to be imaged 40 (i.e. a subject to be examined) with radiation (here, X-rays). The radiation generation control unit 31 controls generation of radiation based on an imaging protocol in accordance with the control of the radiation imaging control unit 20. Specifically, the radiation generation control unit 31 applies a voltage to the radiation source 30 to generate radiation in accordance with imaging conditions (e.g. parameters such as tube current, tube voltage, and irradiation time) corresponding to the imaging protocol.

The radiation imaging control unit 20 oversees and controls radiation imaging processing based on the imaging protocol. The radiation imaging control unit 20 also performs image processing on a radiographic image obtained from the radiation imaging apparatus 100. Image processing includes tone processing, frequency processing, and the like, and is performed using image processing parameters according to the imaging protocol. The display unit 21 displays information such as a system state to the operator. The display unit 21 may be a display, for example. For example, the display unit 21 can display an examination order received from the outside, or an examination order created by the operator of the radiation imaging apparatus 100. The operation unit 22 acquires an instruction from the operator. The operation unit 22 may be a keyboard, a mouse, or various buttons, for example. For example, the operator can input an operation instruction to the radiation imaging apparatus 100 via the operation unit 22. The radiation imaging apparatus 100 detects radiation that has been transmitted through the subject to be imaged 40 as charges that correspond to the transmitted radiation dose, generates a radiographic image, which is image data, and transfers the radiographic image to the radiation imaging control unit 20.

Configuration of Radiation Imaging Apparatus

Figure 2A:
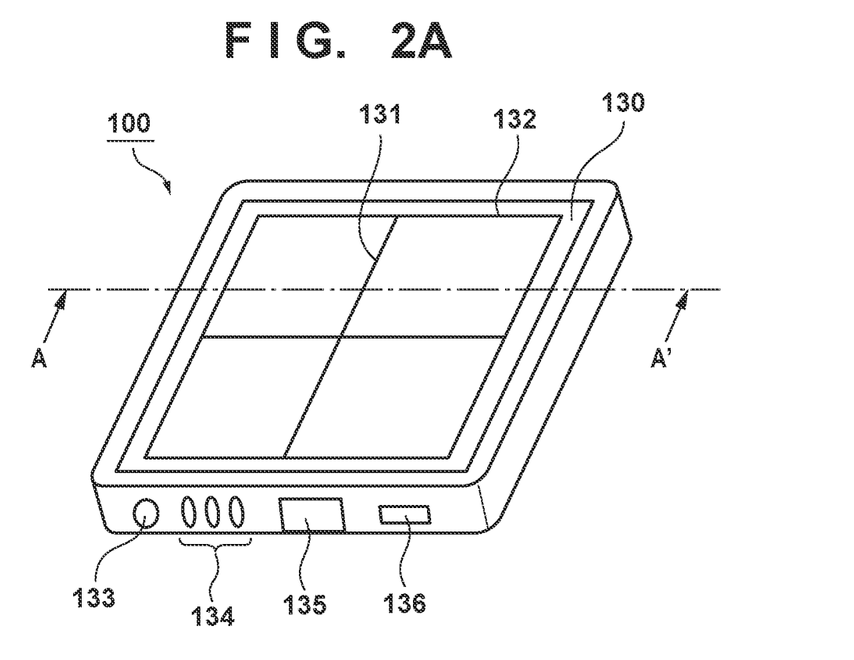
FIGS. 2A and 2B show an example configuration of the radiation imaging apparatus according to Embodiment 1.
Figure 2B:
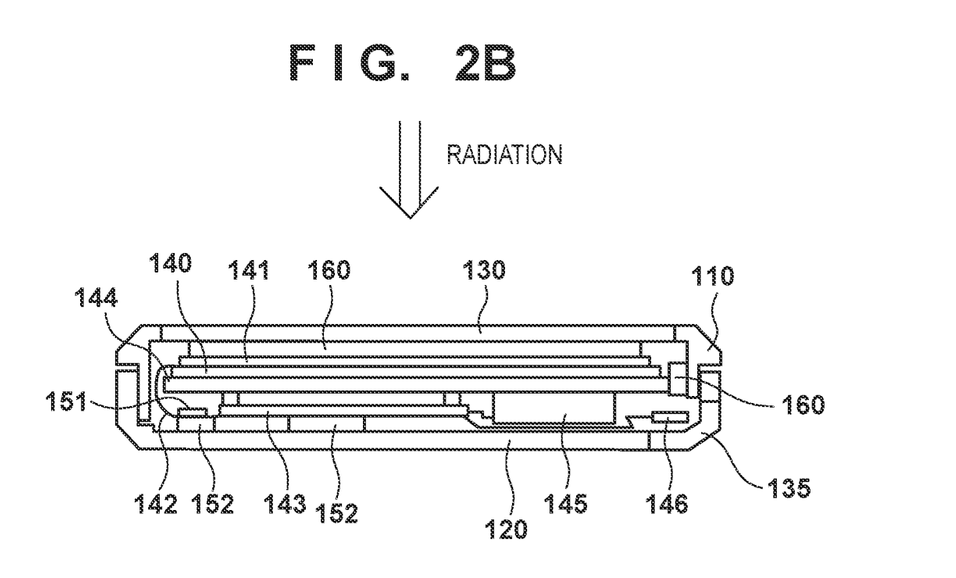

FIGS. 2A and 2B show a configuration of the radiation imaging apparatus 100 according to Embodiment 1. FIG. 2A is a perspective view of the radiation imaging apparatus 100 according to this embodiment as viewed from a radiation incident surface, and FIG. 2B is a cross-sectional view of FIG. 2A taken along a line A-A'. The housing of the radiation imaging apparatus 100 is constituted by a front housing 110, a rear housing 120, and a radiation-transmitting plate 130. The front housing 110 and the rear housing 120 can be made of a material of a low specific gravity, such as aluminum, a magnesium alloy, or CFRP, to reduce the weight of the radiation imaging apparatus for the purpose of securing the strength against a fall, an impact, or the like, and reducing the load during transportation. The radiation-transmitting plate 130 is made of CFRP, for example. Indicators 131 and 132 for indicating the reading center and reading area in a sensor panel 140 are provided on the radiation-transmitting plate 130.

A side face of the radiation imaging apparatus 100 is provided with a switch 133, a state display unit 134, a wireless communication unit 135, and a wired communication connection unit 136. Also, the radiation imaging apparatus 100 contains a battery 145. The battery 145 may be removable so as to be able to be replaced with a charged battery when the remaining battery capacity is low. The radiation imaging apparatus 100 performs an imaging operation using power supplied from the battery 145, and can be used in a wireless state by communicating with the radiation imaging control unit 20 from the wireless communication unit 135 using a built-in antenna 146. If the wireless connection state is poor, wired communication may alternatively be performed by connecting a cable (not shown) to the wired communication connection unit 136. Power can also be supplied in a wired manner when, for example, the remaining capacity of the battery 145 is insufficient. The switch 133 can be used to perform an operation to turn on and off the power of the radiation imaging apparatus 100, an operation to switch an imaging state (a ready state), and the like. The state display unit 134 displays a power-on/off state, the remaining capacity of the battery 145, and the like, through the color of the light, a lighted/flashing/unlighted state, or the like.

The sensor panel (radiation sensor) 140 for converting incident radiation to a charge signal (electrical signal), in which photoelectric conversion elements are formed on a glass substrate, is arranged inside the radiation imaging apparatus 100. A phosphor 141, which converts radiation to visible light, is configured on a surface of the sensor panel 140 on the photoelectric conversion element side. CsI or the like is preferably used as the phosphor 141. The phosphor 141 emits light due to radiation with which the radiation imaging apparatus 100 is irradiated, and the photoelectric conversion elements of the sensor panel 140 convert the emitted light to a few charge signals. These charge signals are used to form an image. Note that the method for converting radiation to charge signals is not limited to the aforementioned one, and for example, a sensor of a direct conversion type that directly converts radiation to charge signals, such as a-Se, may alternatively be used. The charge signals generated (acquired) in the sensor panel 140 are connected, via a flexible board 142, to the integrated circuit 151, which is contained on this flexible board 142. The integrated circuit 151 amplifies a few charge signals, performs A/D conversion thereon, and thus makes the charge signals into digital image signals. These digital image signals are further processed within an electrical circuit board 143 and are transferred to the radiation imaging control unit 20.

A rigid base 144 is adhered to the sensor panel 140 on the side opposite to the radiation incident surface to support the sensor panel 140 such that the sensor panel 140 is not deformed or cracked due to a load applied from the outside, vibrations occurring during transportation, or the like. Also, a radiation insulating member (not shown), which works to, for example, suppress deterioration of radiation on the electrical circuit board 143 and/or remove scattered lines from the rear side of the radiation imaging apparatus 100, is attached to the base 144 as required. The radiation insulating member is made of a material of a high specific gravity, such as molybdenum, iron, or lead, for example. Buffer materials 160 are provided as appropriate between the housing of the radiation imaging apparatus 100 and the members provided inside thereof, and an effect of distributing the load applied from the outside and an effect of buffering an impact are achieved. The buffer materials 160 are porous materials made of silicon or urethane, or materials made of a silicone gel or the like, for example.

During radiation imaging, the integrated circuit 151 and the electrical circuit board 143, which are electronic components that perform processing for the charge signals (electrical signals) obtained by the sensor panel 140, generate heat, and the temperature thereof may increase. If the temperature of the integrated circuit 151 and the electrical circuit board 143 increases excessively, there is a concern that the circuits may be broken, and if the temperature of the sensor panel 140 is nonuniform in the surface thereof, there is a concern that unevenness may occur in the image. For this reason, the heat needs to be transferred to the housing and discharged to the outside of the radiation imaging apparatus 100. Thus, heat conduction members 152 are arranged between the integrated circuit 151 and the rear housing 120 and between the electrical circuit board 143 and the rear housing 120. A silicone rubber sheet, heat conductive grease, heat radiation adhesive, or the like is used as each heat conduction member 152.

Figure 3A:
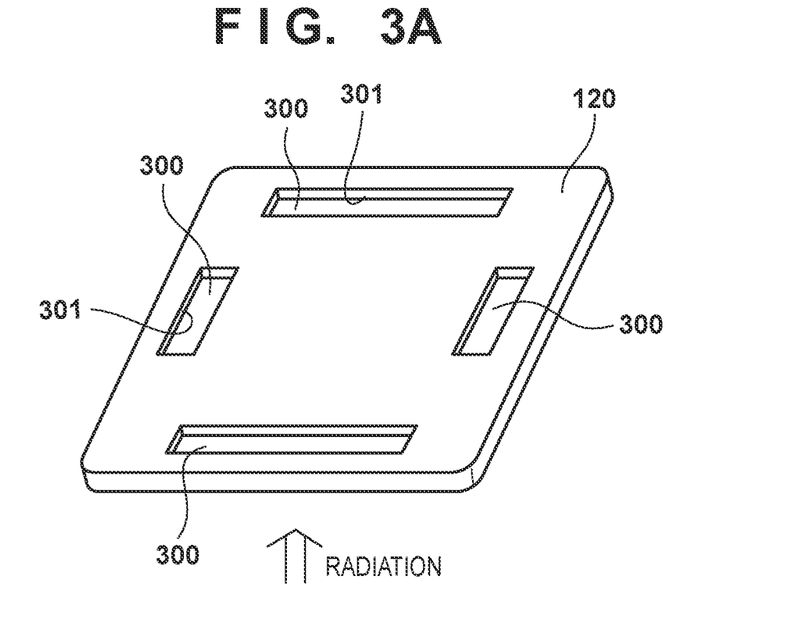
FIGS. 3A and 3B show a structural example of a holding portion according to Embodiment 1.
Figure 3B:
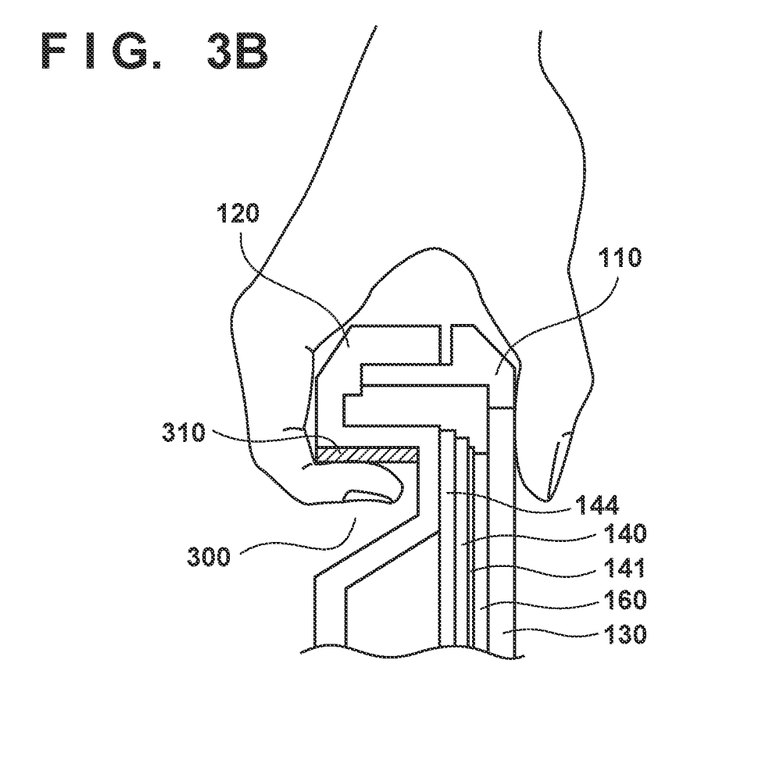

The radiation imaging apparatus 100 according to this embodiment has a structure in which holding portions, each of which has a recessed form, are provided in the back face (on the rear housing 120 side) to improve the portability of the apparatus. The back face is made of a uniform material. FIGS. 3A and 3B show a structural example of the holding portions provided in the back face of the radiation imaging apparatus 100 according to this embodiment. FIG. 3A is a perspective view as viewed from the back face of the radiation imaging apparatus 100, and FIG. 3B is a schematic cross-sectional view that illustrates a cross-sectional structure of a holding portion.

As shown in FIG. 3A, recessed holding portions 300 are provided at positions close to side faces of the housing in the back face of the radiation imaging apparatus 100 according to this embodiment. By arranging the holding portions near the side faces, the radiation imaging apparatus 100 can be held in various orientations and thus can be readily handled. Considering the typical size of a hand of a person, the holdability of the holding portions 300 can be increased by configuring the holding portions 300 such that a portion of each holding portion 300 or the deepest area thereof is located within 60 mm from the corresponding closest side face of the housing. Also, the depth of the recess of each holding portion 300 is greater than the depth of the centroid position of the radiation imaging apparatus in the thickness direction thereof, or is greater than or equal to half the thickness of the radiation imaging apparatus 100 that can be regarded as being substantially the same as the depth of the centroid position. In this embodiment, the thickness of the imaging apparatus is 13 mm to 16 mm in order to conform to the standard dimensions of general imaging cassettes as defined by JISZ4905. In this case, the maximum depth may be greater than 6.5 mm to 8.0 mm. Also, of the faces that form the recess of each holding portion 300, a holding face 301 that opposes the closest side face (i.e. a face portion closest to the side face) may form an angle of 120° or less with respect to the back face of the housing. Thus, holding force can be applied without relying on frictional force.

As mentioned above, the heat within the radiation imaging apparatus 100 is transferred so as to be released to the rear housing 120. Thus, the temperature of the back face of the radiation imaging apparatus 100 is likely to increase. Particularly, each of the holding faces 301 may be a portion to be touched as fingers are always hooked thereon when the radiation imaging apparatus 100 is handled, and it is therefore highly probable that an operator and/or a subject to be examined feels uncomfortable if the operator and/or the subject to be examined feels that the temperature of the holding face 301 is high. In this embodiment, a non-heat conductive sheet 310 having a lower heat conductivity than that of the rear housing 120 is attached to each holding face 301, which serves as at least one of the faces that form the recess of the holding portion 300. A rubber sheet, a resin sheet, a porous material sheet, or the like is used as the non-heat conductive sheet 310. Even if the temperature increases by the same amount, if the holding portion 300 is touched via a material with a low heat conductivity, the sensable temperature can be lowered. Also, the temperature of the touched portion can be lowered by heat resistance between the rear housing 120 and the non-heat conductive sheet 310. These effects make it possible to lessen the discomfort when fingers are hooked at the holding face 301.

As described above, this embodiment can provide a radiation imaging apparatus with good holdability and a structure that makes the operator and/or the subject to be examined feel less uncomfortable.

Embodiment 2

Figure 4A:
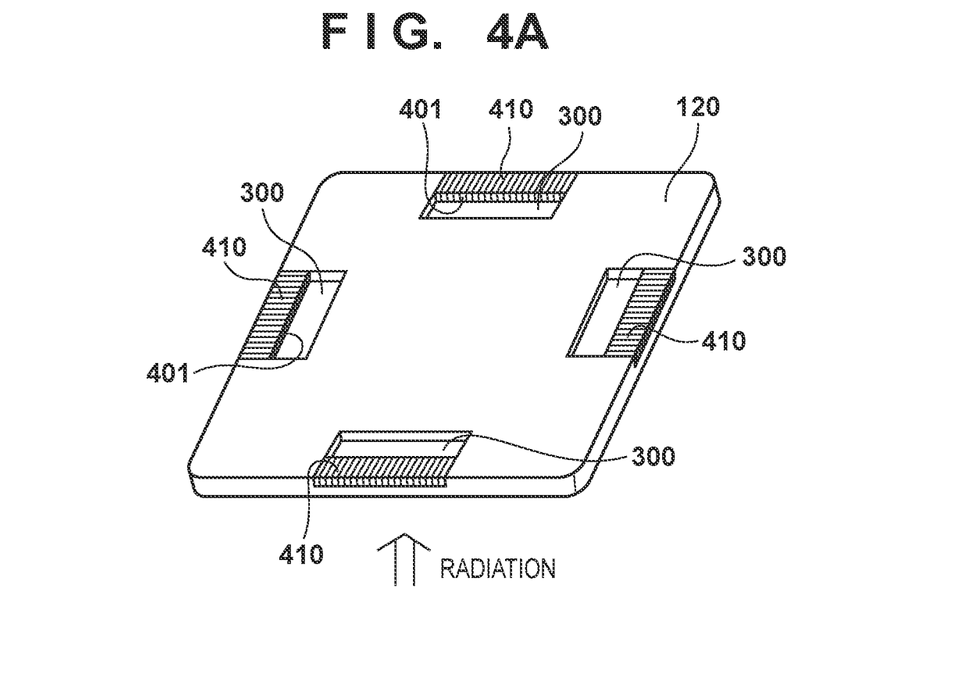
FIGS. 4A and 4B show a structural example of a holding portion according to Embodiment 2.
Figure 4B:
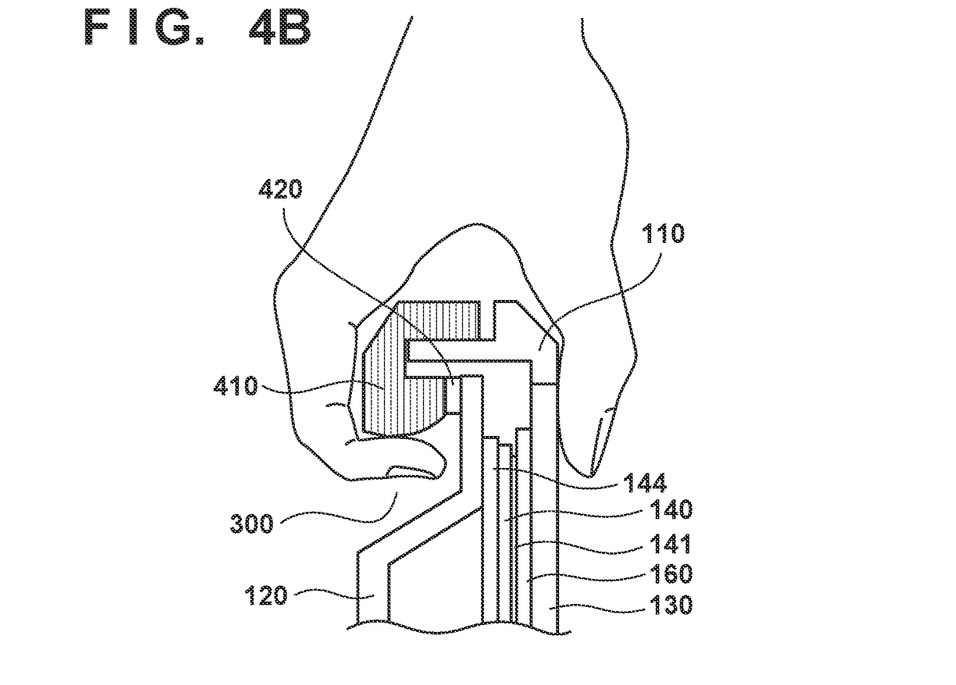

This embodiment will describe a structural example of a holding portion that has better holdability than that in Embodiment 1 and can lessen discomfort when being handled. Differences from Embodiment 1 will be described below. FIGS. 4A and 4B show a structure of holding portions provided in the back face of the radiation imaging apparatus 100 according to this embodiment. FIG. 4A is a perspective view as viewed from the back face of the radiation imaging apparatus 100, and FIG. 4B is a schematic cross-sectional view that illustrates a cross-sectional structure of a holding portion.

In this embodiment, to form holding faces 401 of recesses to be held in an exterior housing of the radiation imaging apparatus 100, holding components 410 are used as predetermined holding portion forming components that are made of a material with a lower heat conductivity than that of the rear housing 120. The holding components 410 may be made of a material such as a resin or a rubber, which is a material with a lower heat conductivity than that of the rear housing 120. By using the holding components 410 made of this type of material, the sensable temperature can be lowered when the radiation imaging apparatus 100 is used, similarly to Embodiment 1. The holding components 410 are attached to the rear housing 120 via heat insulating double-sided tapes 420, for example. Heat insulating sheets may alternatively be used in place of the double-sided tapes 420. Compared with Embodiment 1, the distance of a heat-conducting path from the rear housing 120 to each holding face 401 can be readily secured, and thus, the temperature of the holding faces 401 can be readily lowered. Note that the holding components 410 may be extended to the side faces of the radiation imaging apparatus 100. In this case, not only the holding faces 401 but also portions that may be touched by a hand or the like when being held are made of a material with a low heat conductivity, and thus, discomfort felt by the operator and/or the subject to be examined can be further lessened.

Since the material for forming the rear housing 120, such as aluminum, magnesium, or CFRP, is ordinarily processed using a mold by means of die casting, pressing, or the like, a complicated shape or a so-called undercut shape that cannot be released from a mold cannot be formed. By providing the holding components 410 as separate members, an R shape or a shape with recesses and projections at which fingers to hold the holding components 410 can be readily hooked can be formed relatively freely. Also, if the holding components 410 are made of a rubber material, the frictional force when they are held increases, whereas, if the holding components 410 are made of a soft material, they can be deformed corresponding to the fingers. In terms of these points, the holdability can be improved compared with Embodiment 1 by attaching the holding components 410 that are members separate from the rear housing 120.

As described above, this embodiment can provide a radiation imaging apparatus capable of further lessening discomfort felt by the operator and/or the subject to be examined, while improving holdability.

Embodiment 3

Figure 5A:
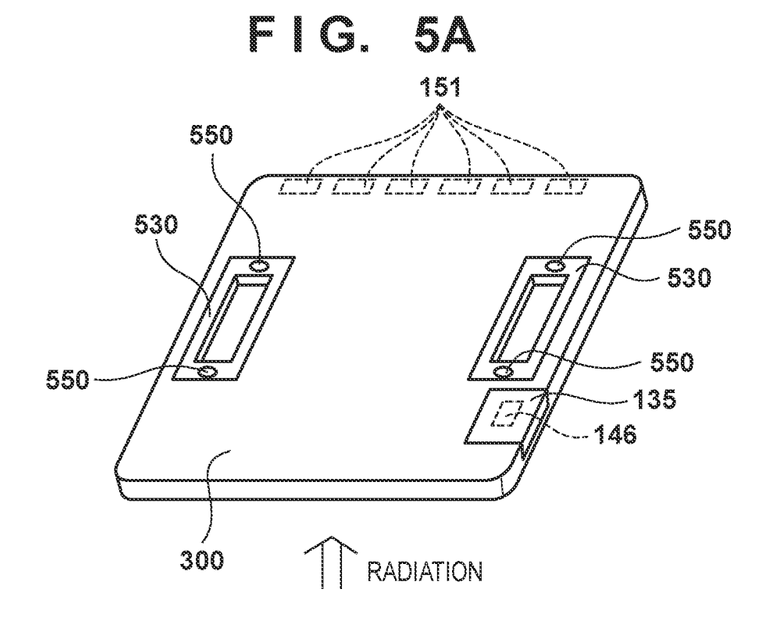
FIGS. 5A and 5B show a structural example of a holding portion according to Embodiment 3.
Figure 5B:
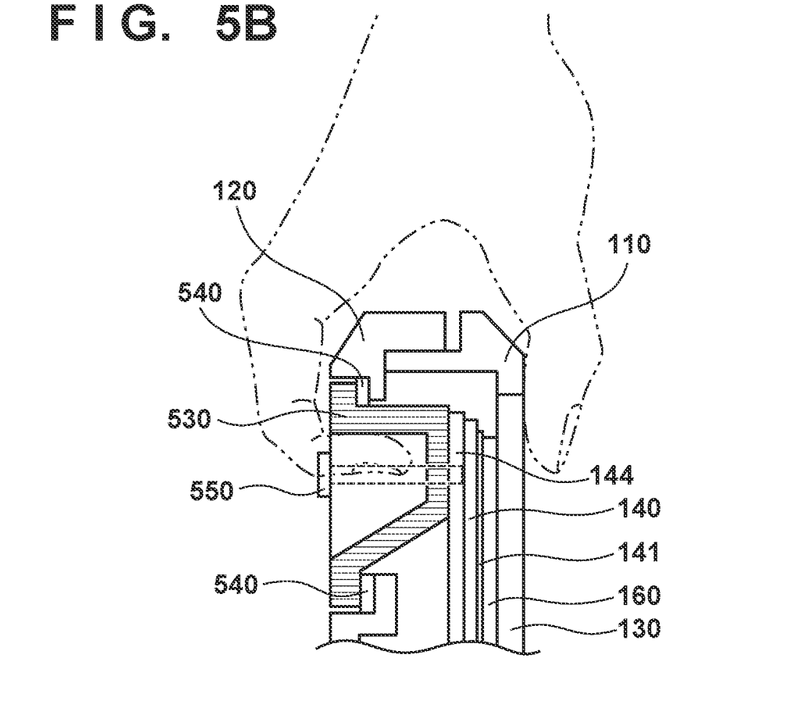

This embodiment will describe a relationship between the constituent elements of the radiation imaging apparatus 100 in a structure in which holding components are provided. FIGS. 5A and 5B show a structural example of the holding portions provided in the back face of the radiation imaging apparatus 100 according to this embodiment. FIG. 5A is a perspective view as viewed from the back face of the radiation imaging apparatus 100, and FIG. 5B is a schematic cross-sectional view that illustrates a cross-sectional structure of a holding portion.

In this embodiment, recesses to be held are formed in an exterior housing of the radiation imaging apparatus 100, using holding components 530. The holding components 530 are fixed via heat insulating double-sided tapes 540 so as to be fitted to open-hole portions that are provided in the rear housing 120. The holding components 530 may be made of a resin, a rubber material, or the like, as mentioned in Embodiment 2. That is to say, the holding components 530 are made of a non-conductive material. For this reason, the holding components 530 do not have an effect of shielding the open hole portions provided in the rear housing 120, and may cause electromagnetic stress from the outside of the apparatus to enter the inside of the apparatus. If such electromagnetic stress appears as noise in a radiation image signal or a control signal for the imaging operation, it may cause an image noise, an erroneous operation, or the like. Particularly, the charge signals for forming an image that are read out from the sensor panel 140 are very small signals, and are easily affected by electromagnetic stress.

Considering the circumstances, the radiation imaging apparatus 100 according to this embodiment is configured such that the aforementioned electromagnetic stress does not reach a portion where the charge signals are in a state before being amplified and subjected to A/D conversion. Specifically, in the radiation imaging apparatus 100 according to this embodiment, the holding components 530 and the open holes in the rear housing 120 to which the holding components 530 are to be fitted are not provided near the side where the flexible board 142 for connecting the charge signals to the electrical circuit board (i.e. for connecting the integrated circuit 151 to the sensor panel 140), and the integrated circuit 151 for amplifying the charge signals and performing A/D conversion thereon, are arranged. In this embodiment, the holding components 530 are provided near two opposing sides, and the flexible board 142 and the integrated circuit 151 are arranged near a side perpendicular to these sides. The integrated circuit 151, which generates a large amount of heat, is disposed away from a holding portion 300, and thus, discomfort felt by the operator and/or the subject to be examined can be further reduced. Similarly, the electrical circuit board, which generates a large amount of heat, is arranged in an area distant from a holding portion 300 (e.g. near a side face different from the side faces closest to the holding portion 300, or near a side face farthest from the holding portion 300), and thus, discomfort felt by the operator and/or the subject to be examined can be further reduced.

Also, the antenna 146 may also be provided near any of the holding components 530. Specifically, a holding component 530 and an open hole in the rear housing 120 to which this holding component 530 is to be fitted are provided near a side where the antenna 146 is arranged. Wireless communication using the antenna 146 is performed between the radiation imaging apparatus 100 and an external device via the wireless communication unit 135 provided in the housing. The wireless communication unit 135 is formed by providing an open hole in the housing, which is made of a conductive material, and attaching a non-conductive cover thereto. Here, by providing a holding component 530 near the antenna 146, wireless communication is enabled not only via the wireless communication unit 135 but also via the region around the holding component 530, and thus, communication stability can be increased. A configuration is also possible where the wireless communication unit 135 is not provided, and wireless communication is performed only via the region around a holding component 530. By arranging the antenna 146, which is a component that generates a small amount of heat, in an area near a holding portion 300 (e.g. near the same side face as that of the holding portion 300, or near the side face closest to the holding portion 300), it also contributes to arranging the electrical circuit board, which generates a large amount of heat, in an area distant form the holding portion (e.g. near a side face different from the holding portion 300, or near the side face farthest from the holding portion 300). The non-heat conductive sheet 310 may be formed near a side face of the housing that is closest to the antenna.

Also, the housing of the radiation imaging apparatus 100, which is constituted by the front housing 110, the rear housing 120, the radiation-transmitting plate 130, and the holding components 530, can be fixed to the internal base 144 at the portions of the holding components 530. In this embodiment, the housing is fixed using screws 550. The fixing method may alternatively be selected from any methods including adhesion and fixing using rivets. As a result of the housing and the internal components being integrated via the holding components 530 that are made of a non-conducive material, a configuration can be achieved in which electrical stress, such as electrostatic discharging, from the outside is not conducted to the inside. By arranging the screws 550, which are made of a highly heat-conductive material, in the holding faces and areas from the holding faces to the side faces of the apparatus, i.e. outside the area that may be touched when the apparatus is handled, discomfort felt by the operator and/or the subject to be examined can also be lessened.

As described above, this embodiment can provide a radiation imaging apparatus that is resistant to electromagnetic stress and electrostatic discharging from the outside and is capable of stable wireless communication, while lessening discomfort felt by the operator and/or the subject to be examined.

Although the above embodiments employ a configuration in which the front housing 110 and the rear housing 120 encompass the sensor panel 140 and the electronic circuits such as the integrated circuit 151 and the electrical circuit board 143, a configuration may alternatively be employed in which these components are encompassed by one housing. Also, the shape of the recess that forms each holding portion is not limited to that shown in the drawings. For example, the shape of a recess that forms each holding portion may be a shape that does not have a face parallel to the back face of the housing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-144028 filed on Jul. 31, 2018 which is hereby incorporated by reference herein in its entirety.

What is claimed is:

1. A radiation imaging apparatus, comprising:
   a radiation sensor configured to convert incident radiation to an electrical signal;
   a housing that encompasses the radiation sensor, said housing having a radiation incident surface and a back face on a side opposite to said radiation incident surface, said back face comprising a holding portion shaped as a recess formed therein; and
   a member having a lower heat conductivity than a heat conductivity of the back face arranged in the recess configured as an outer piece of the back face.

2. The radiation imaging apparatus according to claim 1, wherein the member is arranged in a face that is one of faces forming the recess and opposes a side face of the housing that is closest to the recess.

3. The radiation imaging apparatus according to claim 1, further comprising an electronic component configured to process the electrical signal obtained by the radiation sensor; and
   a heat conduction member provided between the electronic component and the housing.

4. The radiation imaging apparatus according to claim 3, wherein the holding portion is located on a side face side of the housing that is farthest from the electronic component.

5. The radiation imaging apparatus according to claim 1, wherein the recess has a depth that is greater than a depth of a centroid position of the radiation imaging apparatus in a thickness direction thereof, or that is at least half a thickness of radiation imaging apparatus.

6. The radiation imaging apparatus according to claim 1, wherein a portion of the holding portion is located within at least 60 mm from a side face of the housing that is closest to the holding portion.

7. The radiation imaging apparatus according to claim 1, wherein an angle formed between the back face of the housing and a face that is one of faces forming the recess and is closest to a side face of the housing is 120° or less.

8. The radiation imaging apparatus according to claim 1, wherein the member extends to a side face of the housing.

9. The radiation imaging apparatus according to claim 1, wherein the back face of the housing is made of a uniform material.

10. A radiation imaging apparatus, comprising:
    a radiation sensor configured to convert incident radiation to an electrical signal;
    a housing that encompasses the radiation sensor, said housing having a radiation incident surface and a back face on a side opposite to said radiation incident surface, said back face comprising a holding portion shaped as a recess formed therein; and
    a member having, a lower heat conductivity than a heat conductivity of the back face arranged in the back face at a position corresponding to the holding portion, wherein
    the member is fixed to the radiation imaging apparatus via a heat insulating member.

11. A radiation imaging apparatus, comprising:
    a radiation sensor configured to convert incident radiation to an electrical signal;
    a housing that encompasses the radiation sensor, said housing having a radiation incident surface and a back face on a side opposite to said radiation incident surface, said back face comprising a holding portion shaped as a recess formed therein;
    a wireless communication antenna provided inside the housing; and
    a member having a lower heat conductivity than a heat conductivity of the back face arranged in the back face at a position corresponding to the holding portion, wherein
    the member is located near a side face of the housing that is closest to the antenna.

12. A radiation imaging apparatus, comprising:
    a radiation sensor configured to convert incident radiation to an electrical signal;
    a housing that encompasses the radiation sensor, said housing having a radiation incident surface and a back face on a side opposite to said radiation incident surface, said back face comprising a holding portion shaped as a recess formed therein;
    a base provided in the housing that supports the radiation sensor; and
    a member having a lower heat conductivity than a heat conductivity of the back face arranged in the back face at a position corresponding to the holding portion, wherein
    the housing and the base are fixed via the member.

13. A radiation imaging apparatus, comprising:
    a radiation sensor configured to convert incident radiation to an electrical signal;
    a housing that encompasses the radiation sensor, said housing having a radiation incident surface and a back face on a side opposite to said radiation incident surface, said back face comprising a holding portion shaped as a recess formed therein; and
    a member having a lower heat conductivity than a heat conductivity of the back face arranged in the recess and a peripheral region thereof so as to cover the recess, wherein
    the member is fixed to the back face in the peripheral region.

14. The radiation imaging apparatus according to claim 13, wherein the housing comprises a magnesium alloy, and the member comprises a resin.

15. The radiation imaging apparatus according to claim 13, further comprising an electronic component configured to process the electrical signal obtained by the radiation sensor, wherein
    the member is arranged so as to cover a recess formed on a side face side different from a side face side of the housing that is closest to the electronic component.

16. The radiation imaging apparatus according to claim 15, wherein the electronic component comprises an integrated circuit configured to perform A/D conversion of a signal from the radiation sensor, and a flexible board connecting the integrated circuit to the radiation sensor.

17. A radiation imaging apparatus, comprising:
    a radiation sensor configured to convert incident radiation to an electrical signal;
    a housing that encompasses the radiation sensor, said housing having a radiation incident surface and a back face on a side opposite to said radiation incident surface, said back face comprising an open-hole portion; and
    a member having a lower heat conductivity than a heat conductivity of the back face arranged in the open-hole portion so as to form a recess as a holding.

18. The radiation imaging apparatus according to claim 17, wherein the member is arranged in the open-hole portion and a peripheral region thereof so as to cover the open-hole portion, and the member is fixed to the back face in the peripheral region.

19. The radiation imaging apparatus according to claim 18, wherein the member is fixed to the back face in the peripheral region using a double-sided tape.

* * * * *